United States Patent [19]

Doorakian et al.

[11] 4,340,761

[45] Jul. 20, 1982

[54] PREPARATION OF PHOSPHONIUM PHENOXIDE SALTS

[75] Inventors: George A. Doorakian, Bedford; Wanda S. Smith, Framingham, both of Mass.

[73] Assignee: The Dow Chemical Company, Midland, Mich.

[21] Appl. No.: 209,640

[22] Filed: Nov. 24, 1980

[51] Int. Cl.$^3$ .............................................. C07F 9/54
[52] U.S. Cl. .................................................... 568/11
[58] Field of Search ......................................... 568/11

[56] References Cited

U.S. PATENT DOCUMENTS

| | | | |
|---|---|---|---|
| 2,102,103 | 12/1937 | Urbain et al. | 568/11 |
| 3,325,546 | 6/1967 | Harp | 568/11 |
| 4,093,650 | 6/1978 | Doorakian et al. | 568/11 |

OTHER PUBLICATIONS

Schindlbauer, Ber. 96 2109 (1963).

Primary Examiner—Helen M. S. Sneed
Attorney, Agent, or Firm—M. L. Glen

[57] ABSTRACT

A tetrahydrocarbylphosphonium phenoxide salt is prepared by reacting a tetrahydrocarbylphosphonium halide salt with an alkali metal or ammonium hydroxide in a liquid reaction medium in the presence of at least an equivalent amount of a phenol. This method of preparation is especially effective where the hydroxide salt of the tetrahydrocarbylphosphonium is unstable. For example, benzyltriphenylphosphonium salt of bisphenol A complexed with bisphenol A is prepared by adding 1 equivalent of sodium hydroxide to a methanol solution containing 1 equivalent of benzyltriphenylphosphonium bromide and 2 equivalents of bisphenol A at 30° C.

6 Claims, No Drawings

PREPARATION OF PHOSPHONIUM PHENOXIDE SALTS

BACKGROUND OF THE INVENTION

This invention relates to the preparation of a tetrahydrocarbylphosphonium phenoxide salt. More specifically, a process is described wherein a tetrahydrocarbylphosphonium halide is reacted with an alkali metal or ammonium hydroxide in the presence of a phenol.

Canadian Pat. No. 833,674 teaches a process for preparing an organosilicon polymer in the presence of quaternary phosphonium salts of monohydric phenols. However, this patent fails to disclose any method for preparing these salts.

G. M. Kosolapoff et al., Organic Phosphorus Compounds, Vol. 2, pp. 200–202 (1972), discloses that when phosphonium hydroxides are stable at least for a short time, they can be converted to salts having other anions by adding the appropriate acid. This article does not teach anything explicit pertaining to the preparation of phosphonium phenoxides.

SUMMARY OF THE INVENTION

It has now been discovered that a tetrahydrocarbylphosphonium phenoxide salt is prepared in a process comprising reacting by contacting a tetrahydrocarbylphosphonium halide salt in the presence of a phenol compound with an alkali metal or ammonium hydroxide in a liquid reaction medium, so as to effect conversion of the tetrahydrocarbylphosphonium halide salt to the corresponding tetrahydrocarbylphosphonium salt of the phenol compound.

These phosphonium phenoxide salts can be represented by the formula

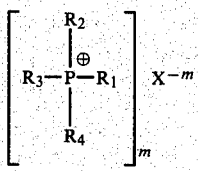

I wherein $R_1$–$R_4$ are each independently hydrocarbyl or inertly-substituted hydrocarbyl, "X" is a conjugate base of an aromatic carbocyclic compound, said compound bearing at least one nuclear hydroxyl group, and "m" is the valence of the anion "X". The tetrahydrocarbylphosphonium phenoxide salts can be complexed with one or more equivalents of an aromatic carbocyclic hydroxyl compound, $H_mX$, wherein X and m are defined above.

DETAILED DESCRIPTION OF THE INVENTION

The reactants in the instant process are known classes of compounds. The tetrahydrocarbylphosphonium halide is represented by the formula

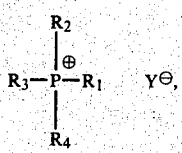

wherein Y is chloride, bromide or iodide, preferably chloride or bromide, and $R_1$–$R_4$ are as described hereinbefore. Preferably, $R_1$–$R_4$ are each independently phenyl, benzyl, alkyl or inertly-substituted alkyl having from 1 to 12 carbon atoms. More preferably, $R_1$–$R_4$ are each preferably, benzyl, phenyl or $C_1$–$C_4$ alkyl. Most preferably, $R_1$–$R_3$ are each phenyl and $R_4$ is a $C_1$–$C_4$ alkyl or benzyl.

The alkali metal hydroxide reactant is preferably sodium or potassium hydroxide. The alkali metal or ammonium hydroxide is conveniently employed as an aqueous or lower ($C_1$ to $C_4$) alkanol solution to promote good heat transfer and good dissolution of this reactant.

The phenol compound is an organic compound having an aromatic mono- or polycyclic hydrocarbon nucleus bearing one or more hydroxyl groups. Representative phenol compounds include phenol, α- and β-naphthol, o-, m-, or p-chlorophenol, 2-hydroxybiphenyl, alkylated derivatives thereof (e.g., o-methyl-, 3,5-dimethyl-, p-t-butyl and p-nonyl-phenol), resorcinol, hydroquinone, phenolphthalein, etc. The term phenol also includes well-known compounds represented by the following formula

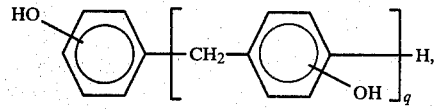

wherein q is an integer of from 1 to 11. Preferred as the phenol reactant are polyhydric phenols bearing from 2 to 6 nuclear hydroxyl groups and having from about 12 to about 30 carbon atoms. These preferred phenol compounds include phenolphthalein, 2,4′,4″-tri(hydroxyphenyl)methane and so-called bisphenols.

Particularly preferred are polyhydric phenols corresponding to the formula

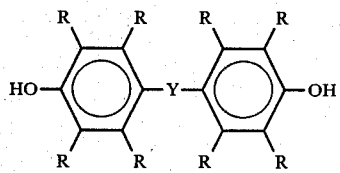

wherein each R independently is a hydrogen, halogen, hydrocarbyl, inertly-substituted hydrocarbyl or hydrocarbyloxy group, and Y is a single covalent bond, oxygen, sulfur, —CO—, —SO—, —SO₂—, lower alkylene or alkylidene of from 1 to 6 carbon atoms, inclusive. More preferably, each R independently is hydrogen, chlorine or bromine and Y is a $C_1$–$C_4$ alkylene or alkylidene; most preferably, Y is methylene or isopropylene. The most preferred phenoxide anions and dianions are those derived from bisphenol A (4,4′-isopropylidenediphenol), bisphenol F (4,4′-methylenediphenol), 2,2′,6,6′-tetrachlorobisphenol A, 2,2′,6,6′-tetrabromobisphenol A, bisphenol S (4,4′-sulfonyldiphenol) and 2,2′,6,6′-tetrabromo-4,4′-sulfonyldiphenol.

Another group of preferred polyhydric phenols are products of the known "advancement reaction" of a polyepoxide compound with an excess of a bisphenol compound. These advancement reaction products can be represented by the formula

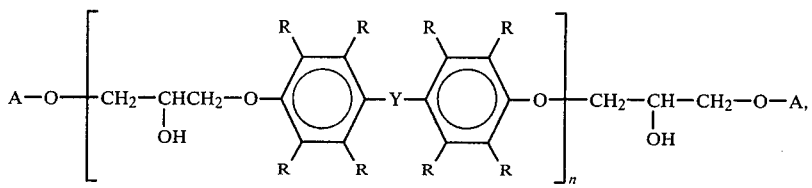

wherein Y and R are as identified hereinbefore, n is an integer of from 1 to about 20 and A is a univalent radical having the formula

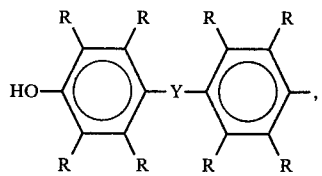

wherein R is defined hereinbefore.

If the phenol reactant has a pKa (of the first hydroxyl group deprotonated) greater than about 7.5, for example bisphenol A (pKa 10.0), then the phosphonium phenoxide product as isolated will generally be in the form of a complex, with an equivalent quantity of the phenol compound. In the case of this complex, the stoichiometry of the reaction requires two equivalents of the phenol for each equivalent of the phosphonium halide salt. On the other hand, if the phenol reactant has a pKa less than about 7.5, for example, 2,2',6,6'-tetrabromo-4,4'-isopropylidenediphenol (pKa 6.8), the stoichiometry of the reaction generally requires only one equivalent of the phenol for each equivalent of the phosphonium halide salt. It is preferred that the phenol compound and the phosphonium halide salt are present in the stoichiometric ratio in the reaction medium, but an excess of either reactant is operable.

The stoichiometry of the reaction requires one equivalent of ammonium or alkali metal hydroxide for each equivalent of the tetrahydrocarbyl phosphonium halide salt to be converted to the corresponding phosphonium phenoxide salt. However, if a stoichiometric excess of the phosphonium halide salt is present relative to the phenol, the equivalents of the hydroxide salt reactant utilized advantageously does not exceed the stoichiometric quantity of the phosphonium halide present relative to the phenol compound present. The aforementioned advantageous ratio minimizes oxidation of the excess phosphonium halide salt to a phosphine oxide. On the other hand, if the phenol and phosphonium halide salt are present in a stoichiometric ratio or an excess of the phenol is present, a stoichiometric excess of the ammonium or alkali metal hydroxide reactant can operably be employed, but confers no substantial advantage.

The reaction is conveniently conducted by introducing the alkali metal or ammonium hydroxide reactant, optionally as an aqueous solution, into a liquid reaction medium containing the phosphonium halide salt reactant and the phenol. Alternatively, the alkali metal or ammonium hydroxide and the phosphonium halide can be contemporaneously added to a liquid medium containing phenol. The liquid reaction medium can operably be neat or can contain a liquid inert organic diluent. The term "inert" means inert in the instant reaction. Suitable diluents include water, lower ($C_1$-$C_4$) alkanols, aromatic hydrocarbons, such as benzene or toluene, and mixtures thereof.

The order of addition or method of contacting the reactants is not critical so long as the phenol reactant is not exhausted while quantities of the phosphonium halide and alkali metal hydroxide reactants still remain. Substantially any reaction temperature from about $-20°$ C. to about $60°$ C. can be used to advantage, preferably $0°$ C. to about $40°$ C. Typically, the reaction rate will be more rapid at higher temperatures within the aforementioned ranges. Lower reaction temperatures than the foregoing are operable, but require uneconomically long reaction times.

The tetrahydrocarbylphosphonium phenoxide salts are generally insoluble in aqueous or alkanol media. Therefore, by selecting the appropriate diluent for the reaction medium, the desired product can be conveniently recovered as a precipitate. Alternatively, the alkali metal or ammonium halide coproduct can first be selectively removed from the reaction medium via a conventional technique, such as filtration from an alkanoic medium or extraction from an aqueous medium and the desired phosphonium phenoxide salt recovered by distillation of the extracted reaction mixture at reduced pressure to remove the volatile components. The reaction to the phosphonium phenoxide salt is essentially quantitative, so if the reactants are employed in stoichiometric amounts the product recovered by distillation at completion of the reaction will be of high purity.

The subject tetrahydrocarbylphosphonium phenoxide salts are useful as catalysts for promoting the reaction between vicinal epoxides and phenols. This utility is described in U.S. patent application Ser. No. 041,567, filed May 21, 1979, the relevant portions of which are incorporated herein by reference.

The following examples are illustrative of the present invention and are not to be construed as limiting the scope thereof in any manner. All parts and percentages are by weight unless otherwise specified.

EXAMPLE 1

A solution of 28.54 grams (0.125 mole) of bisphenol A in 34.0 milliliters (ml) of methanol at 20° C. was added to a stirred reaction mixture of 25 grams of n-butyltriphenylphosphonium bromide in 37.5 ml of methanol. An aqueous solution of 50 percent sodium hydroxide (5.02 grams, 0.0627 mole) at 20° C. was then added to the reaction mixture with cooling and at a slow rate, so that the temperature of the mixture did not exceed 25° C. The reaction mixture was stirred for an additional 10 minutes, followed by the addition of 12.5 grams of deionized water to the mixture and stirring for 60 more minutes. A white crystalline precipitate was recovered by filtration of the reaction mixture. This crude product was washed with deionized water and dried to a weight of 48.4 grams. Conventional methods of analysis were used to identify the product as a 1:2 n-butyltriphenylphosphonium salt complex of bisphenol A. This is termed a 1:2 salt because 1 equivalent of the phosphonium cation is present with 2 equivalents of bisphenol A (whether as a bisphenoxide anion or bisphenol adduct). The yield of the product based on the corresponding phosphonium hydroxide salt (assuming quantitative conversion of the phosphonium halide to the hydroxide salt) was 96 mole percent.

COMPARATIVE EXPERIMENT 1

(Not an embodiment of this invention)

An aqueous solution of 50 percent sodium hydroxide (5.02 grams, 0.0627 mole) at 20° C. was added to a stirred reaction mixture of 25 grams (0.0626 mole) n-butyltriphenylphosphonium bromide in 37.5 ml of methanol cooled to a temperature of 5° C. The rate of sodium hydroxide addition was controlled, so that the temperature of the reaction mixture does not exceed 15° C. After addition of the sodium hydroxide was complete, the temperature of the stirred reaction mixture was permitted to rise to 18° C. over a period of 15 minutes. A solution of 28.54 grams (0.125 mole) of bisphenol A in 34.0 ml of methanol was rapidly added at 20° C. to the stirred reaction mixture. The reaction mixture was stirred for an additional 10 minutes, followed by the addition of 12.5 grams of deionized water to the mixture, and stirring for 60 more minutes. A white crystalline precipitate was recovered by filtration of the reaction mixture. This crude product was washed with deionized water and dried to a weight of 46.0 grams. Conventional methods of analysis were utilized to identify the product as a 1:2 n-butyltriphenylphosphonium salt complex of bisphenol A. The yield of the product based on the corresponding phosphonium hydroxide salt (assuming quantitative conversion to the hydroxide salt) was 92.7 mole percent.

EXAMPLE 2

To a stirred solution of 10.9 grams (0.025 mole) of benzyltriphenylphosphonium bromide in 28.0 ml of methanol was added at 30° C. 11.4 grams (0.05 mole) of bisphenol A. The bisphenol A dissolved producing a transparent, gold-colored solution. An aqueous solution of 50 percent sodium hydroxide (0.025 mole) was added to the reaction mixture at a temperature of from 30°–32° C. The stirring of the mixture was continued under reduced pressure for 1 hour to distill the methanol solvent. A pinkish-white solid precipitated. Phosphorus-31 nuclear magnetic resonance spectroscopy confirmed that no phosphine oxide was present in the product.

A comparative experiment was performed in an identical manner except that the sodium hydroxide solution was added to the phosphonium bromide salt in methanol first and then the solid bisphenol A was added. After about 3 hours of stirring under reduced pressure, the reaction mixture became visibly turbid. Phosphorus-31 nuclear magnetic resonance spectroscopy was used to determine that about 60 mole percent of the phosphorus was present in a phosphine oxide and about 40 mole percent of the phosphorus was present as a phosphonium salt.

What is claimed is:

1. A process for preparing a tetrahydrocarbylphosphonium phenoxide salt comprising reacting by contacting a tetrahydrocarbylphosphonium halide salt in the presence of a phenol compound with an alkali metal or ammonium hydroxide in a liquid reaction medium, so as to effect conversion of the tetrahydrocarbylphosphonium halide to the corresponding tetrahydrocarbylphosphonium salt of the phenol compound or a phenol complex thereof, said phenol compound being represented by the formula

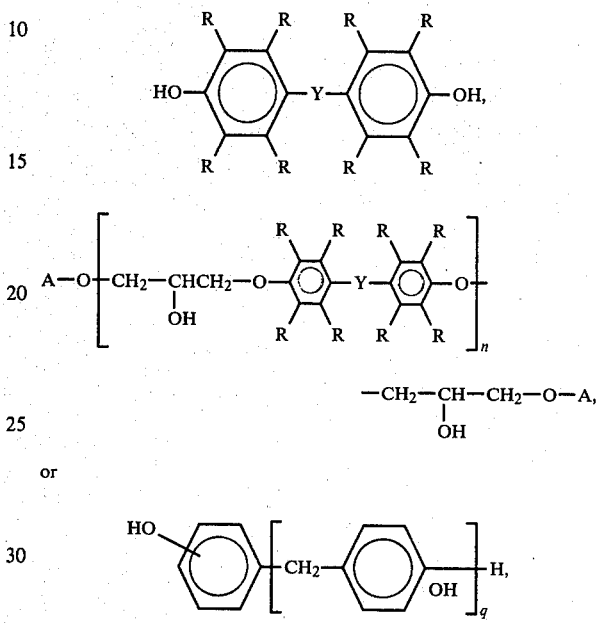

or

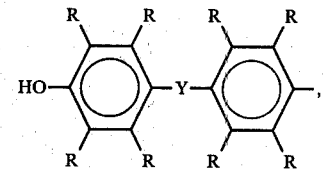

wherein each R independently is a hydrogen, halogen, hydrocarbyl, inertly-substituted hydrocarbyl or hydrocarbyloxy group, Y is a single covalent bond, —O—, —S—, —CO—, —SO—, —SO$_2$—, or lower alkylene or alkylidene of from 1 to 6 carbon atoms, A is n is an integer of from 1 to 20 and q is an integer of from 1 to 11.

2. The process as described in claim 1 wherein the liquid reaction medium contains an inert organic diluent.

3. The process as described in claim 1 wherein the liquid reaction medium is neat.

4. The process as described in claim 1 wherein the tetrahydrocarbylphosphonium halide salt and the phenol are employed in stoichiometric amounts.

5. The process as described in claim 4 wherein the phenol is bisphenol A, bisphenol F, 2,2',6,6'-tetrachlorobisphenol A, 2,2',6,6'-tetrabromobisphenol A, bisphenol S or 2,2',6,6'tetrabromobisphenol S.

6. The process as described in claim 5 wherein the reaction is conducted at a temperature of from about −20° C. to about 60° C.

* * * * *